(12) United States Patent
Hölscher

(10) Patent No.: US 9,157,048 B2
(45) Date of Patent: Oct. 13, 2015

(54) PERFUME

(75) Inventor: Bernd Hölscher, Halle (DE)

(73) Assignee: SYMRISE AG, Holzminden (DE)

( * ) Notice: Subject to any disclaimer, the term of this patent is extended or adjusted under 35 U.S.C. 154(b) by 161 days.

(21) Appl. No.: 13/881,019

(22) PCT Filed: Oct. 25, 2011

(86) PCT No.: PCT/EP2011/068669
§ 371 (c)(1),
(2), (4) Date: Jun. 11, 2013

(87) PCT Pub. No.: WO2012/055875
PCT Pub. Date: May 3, 2012

(65) Prior Publication Data
US 2013/0261036 A1 Oct. 3, 2013

Related U.S. Application Data

(60) Provisional application No. 61/406,274, filed on Oct. 25, 2010.

(51) Int. Cl.
| | |
|---|---|
| *A61K 8/00* | (2006.01) |
| *C11B 9/00* | (2006.01) |
| *A61K 8/37* | (2006.01) |
| *A61Q 13/00* | (2006.01) |
| *C07C 69/708* | (2006.01) |
| *C07C 69/716* | (2006.01) |
| *C07C 69/96* | (2006.01) |
| *A61Q 5/02* | (2006.01) |

(52) U.S. Cl.
CPC .............. *C11B 9/0034* (2013.01); *A61K 8/37* (2013.01); *A61Q 13/00* (2013.01); *C07C 69/708* (2013.01); *C07C 69/716* (2013.01); *C07C 69/96* (2013.01); *A61Q 5/02* (2013.01)

(58) Field of Classification Search
CPC .. C11B 9/0015; C11B 9/0034; C07C 69/708; C07C 69/716; C07C 69/96
USPC ........................................................ 512/22
See application file for complete search history.

(56) References Cited

U.S. PATENT DOCUMENTS

| | | | |
|---|---|---|---|
| 6,384,269 B1 | 5/2002 | Williams | |
| 7,563,925 B1 * | 7/2009 | Levorse et al. | 560/193 |
| 2005/0182273 A1 | 8/2005 | Eh | |
| 2010/0034766 A1 * | 2/2010 | McGee et al. | 424/76.1 |

FOREIGN PATENT DOCUMENTS

| | | | |
|---|---|---|---|
| EP | 1262474 | * | 12/2002 |
| EP | 1398366 | * | 3/2004 |
| FR | 2008167 A1 | | 1/1970 |
| JP | 2011037761 A | | 2/2011 |
| WO | WO0014051 | * | 3/2000 |
| WO | WO2004050602 | * | 6/2004 |
| WO | WO-2008049257 A1 | | 5/2008 |

OTHER PUBLICATIONS

International Search Report with references cited and Written Opinion under Rule 43 PCT attached to the Search Report, PCT Application No. PCT/EP2011/068669.
Examination Report from the European Patent Office issued in parallel European Application No. 11779130.1, received on Mar. 17, 2015.

* cited by examiner

*Primary Examiner* — John Hardee
(74) *Attorney, Agent, or Firm* — Novak Druce Connolly Bove + Quigg LLP

(57) ABSTRACT

The present invention relates to perfumes of general formula (A)

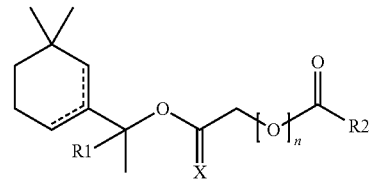

It further relates to the use of the compounds of formula (A) for imparting or intensifying particular odor notes and/or particular odor impressions and a method of producing a perfume mixture or a perfumed product.

18 Claims, No Drawings

PERFUME

CROSS-REFERENCE TO RELATED APPLICATIONS

This application is a national stage application (under 35 U.S.C. §371) of PCT/EP2011/068669, filed Oct. 25, 2011, which claims benefit of U.S. Provisional Application No. 61/406,274, filed Oct. 25, 2010, which are incorporated herein by reference in their entireties.

The present invention relates to perfumes of general formula (A)

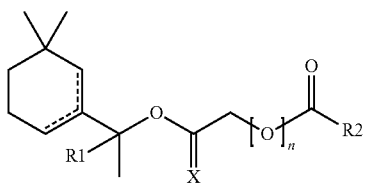

It further relates to the use of the compounds of formula (A) for imparting or intensifying particular odor notes and/or particular odor impressions and a method of producing a perfume mixture or a perfumed product.

Methods for producing compounds of formula (A) are also described.

Although a great many perfumes are already available, in the perfume industry there is still a general demand for new perfumes. Thus, there is a demand for perfumes with musk fragrance notes, which are able (in perfume compositions) to produce, in addition to a musk fragrance note, other interesting odor notes and/or odor impressions and, with their novel or original fragrance properties, to expand the possibilities of the perfumer. In particular there is interest in perfumes with musk fragrance notes that are able to form a harmonious combination with perfumes with a flowery fragrance. Preferably there should be an overlapping of the different olfactory aspects and notes, so as to produce a complex overall odor impression.

For creating novel modern compositions, there is a constant demand for perfumes with special olfactory properties, which are suitable as a basis for the composition of novel modern perfumes with a complex odor character. Preferred sought-after perfumes should have, apart from a musk fragrance note, other notes and aspects that endow them with olfactory character and complexity. Musk perfumes that have, as an additional note, flowery notes and/or can intensify the latter, are of interest for many possible uses of perfumes. Moreover, a number of the known musk perfumes tend to endow perfume compositions with a fragrance impression of only slight radiance. Accordingly, fragrances are of interest which, in combination with musk notes, are additionally able to impart and/or intensify the odor impression in a radiant fashion.

The area of perfume chemistry can be considered to be well-researched in the prior art. In the area of musk perfumes, we may mention in particular Helvetolide/Serenolide, Romandolide and Appelide and derivatives thereof.

Musk perfumes from the stated groups are described in documents DE 102 14 675 A1, WO 2004/050602 A1, EP 0 472 966 A1, WO 00/14051 A1, EP 1 262 474 A1 and EP 1 398 366 A1.

The odor descriptions of the known perfumes, from our own investigations and from the patent literature, can be summarized as follows:

1. Helvetolide (Firmenich): strong musk note of ambrette type. Molecular weight: 284
2. Serenolide (Givaudan): strong musk note. Molecular weight: 296
3. Romandolide (Firmenich): woody, musk-like, of nitro type. Molecular weight: 270
4. Appelide (IFF): musk-like, of nitro type, fruity Molecular weight: 256

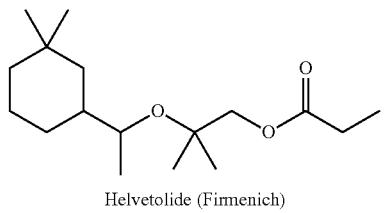

Helvetolide (Firmenich)

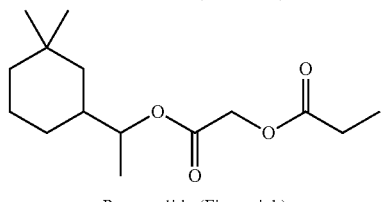

Romanolide (Firmenich)

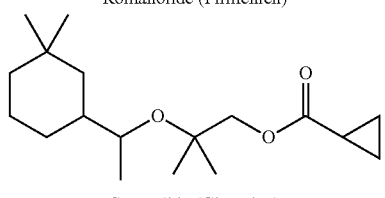

Serenolide (Givaudan)

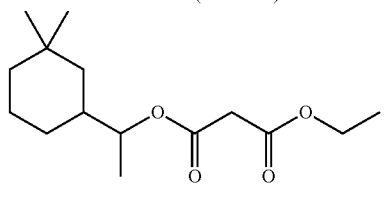

Appelide (IFF)

Work on these classes of compounds relating to derivatization of the side chain was not pursued further in the prior art. This can probably be attributed to the earlier teaching that perfumes with a molecular weight above 294 (exception: Serenolide with 296) are not of interest as perfumes (see G. Ohloff Scent and Fragrances, the Fascination of Odors and their Chemical Perspectives, Springer Verlag Berlin 1994 p. 9). A person skilled in the art would therefore assume that other derivatives of these basic structures, with higher molecular weight, lead to impairment of the olfactory properties.

The search for suitable perfumes, which led to the present invention, was made difficult by the following circumstances:

The mechanisms of odor perception are not adequately known.

The relations between special odor perception on the one hand and the chemical structure of the associated perfume on the other hand have not been investigated sufficiently.

Just slight changes in the structure of a known perfume often cause large changes in the sensory properties and impair compatibility for the human organism.

The sensory effects of interactions with other perfumes cannot be predicted.

The success of a search for suitable perfumes is therefore strongly dependent on the intuition of the person conducting the search.

Against this background, the problem to be solved by the present invention was to provide perfumes which, as well as a musk note, also possess flowery notes (aspects) and/or intensify such notes and are able to impart and/or intensify a radiant odor impression. In addition to this main problem, the perfumes that are to be provided preferably have, as well as their primary (olfactory) properties, an additional or more preferably more than one additional positive secondary properties, for example high stability under specified conditions of use, good adherence, high substantivity, a booster effect also for other than flowery perfumes, a strong blooming and/or the property of imparting and/or intensifying other desirable (subsidiary) odor notes or odor impressions.

According to the invention, the primary problem is solved with a compound of general formula (A)

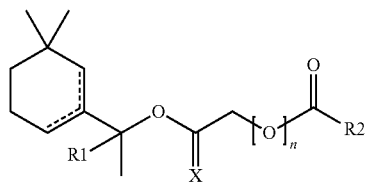

wherein
○○○○ ○ ○ ○○○○ ○ ○ ○○○○ ○ ○ =saturated or unsaturated,
R1=H, methyl or ethyl
X=oxygen or dimethyl
n=0 or 1,
and for the case when n=1, R2
  (i) represents an O—R3 group, wherein R3=an alkyl group with 1 to 4 carbon atoms with a straight, branched or cyclic and saturated or unsaturated chain, or
  (ii) represents a CH2-O—R3 group, wherein R3=an alkyl group with 1 to 4 carbon atoms with a straight, branched or cyclic and saturated or unsaturated chain, or
  (iii) represents a carbonyl-R3 group, wherein R3=an alkyl group with 1 to 4 carbon atoms with a straight, branched or cyclic and saturated or unsaturated chain, or
  (iv) represents a CH2-carbonyl-O—R3 group, wherein R3=an alkyl group with 1 to 4 carbon atoms with a straight, branched or cyclic and saturated or unsaturated chain,
  or for the case when n=0, R2
  (v) represents an alkyl group R3 with 1 to 4 carbon atoms with a straight, branched or cyclic and saturated or unsaturated chain, or
  (vi) represents a CH2-O—R3 group, wherein R3=an alkyl group with 1 to 4 carbon atoms with a straight, branched or cyclic and saturated or unsaturated chain.

Preferably, in the compound according to the invention, R3 is selected from the group consisting of methyl, ethyl, n-propyl and i-propyl, cyclopropyl, n-butyl, i-butyl, tert.-butyl and cyclobutyl.

A compound according to the invention is preferred in which R1=H and/or R3 is selected from the group consisting of methyl, ethyl, n-propyl and i-propyl.

The compounds according to the invention and in particular the aforementioned preferred compounds according to the invention surprisingly all possess, as well as a pleasant musk note, flowery aspects (notes) and/or are able to intensify the latter. Moreover, at the same time, in perfume mixtures they can impart the odor impression radiant and/or intensify it.

The olfactory properties of the compounds according to the invention and in particular of the preferred compounds according to the invention can be described as follows: very strongly radiant, musk-like, uplifting, soft, reminiscent of musk seed oil. The compounds therefore impart a very natural odor impression.

The various olfactory properties could not be predicted for the compounds according to the invention from the prior art. This applies in particular to the combination of musk notes, flowery aspects (notes) and the ability to impart a radiant odor impression and/or to intensify the aforesaid notes/the aforesaid odor impression.

In addition to the primary (olfactory) properties, the compounds according to the invention possess additional positive secondary properties. In particular, relative to similar compounds from the prior art, we may mention improved adherence and high substantivity.

Many of the compounds according to the invention have a molecular weight above 300, so that for the reasons stated above, the industry assumed that molecules of this size do not include any suitable fragrances.

Compounds according to the invention with a molecular weight (MW)≥300 are preferred in many cases. These compounds possess surprisingly strong olfactory properties, with excellent adherence and/or high substantivity.

It is also surprising that, as envisaged in the compounds according to the invention of groups (i), (ii), (iii), (iv) and (vi), the introduction of an oxygen atom in the residue R2 produces flowery notes or intensification thereof for the (or by the) resulting compounds. If derivatives of the aforementioned Helvetolides, Serenolides, Romanolides and Appelides were known from the prior art, which possess the flowery notes, then in the region of the end of the molecule opposite the cyclohexene/hexene ring, these did not have an oxygen atom that is part of an ether or ester group. This applies to oxygen that is provided in the chain run starting from the cyclohexene/hexene ring on the other side of the last oxo group. In this respect, the prior art would even have dissuaded a person skilled in the art, when searching for flowery notes in combination with musk notes, from providing an oxygen in the residue R2 according to formula (A).

Furthermore, it is surprising that the compounds according to the invention possess positive properties such as substantivity, adhesion and biodegradability, but at the same time do not have any unpleasant odor notes, even as a result of hydrolysis.

These properties, too, could not be predicted based on the modifications, which were undertaken contrary to the prior art.

A compound according to the invention is especially preferred that is selected from the group consisting of:
1. methoxyacetic acid-2-[1-(3,3-dimethyl-cyclohexyl)-ethoxy]-2-methyl-propyl ester,
2. ethyl carbonic acid-2-[1-(3,3-dimethyl-cyclohexyl)-ethoxy]-2-methyl-propyl ester,
3. propyl carbonic acid-2-[1-(3,3-dimethyl-cyclohexyl)-ethoxy]-2-methyl-propyl ester,
4. methoxyacetic acid-1-(3,3-dimethyl-cyclohexyl)-ethoxycarbonylmethyl ester,
5. ethyl carbonic acid-1-(3,3-dimethyl-cyclohexyl)-ethoxycarbonylmethyl ester,
6. 4-methoxy-3-oxo-butyric acid-1-(3,3-dimethyl-cyclohexyl)-ethyl ester and
7. 3-oxo-hexanoic acid-1-(3,3-dimethyl-cyclohexyl)-ethyl ester.

TABLE 1

| No.: | Structure | Name | Odor |
|---|---|---|---|
| 1 | 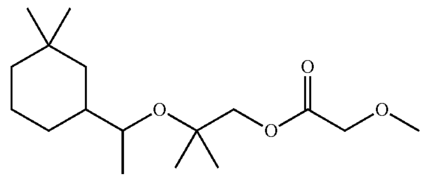 [SMILES: COCC(=O)OCC(C)(C)OC(C)C1CCCC(C)(C)C1] | Methoxyacetic acid-2-[1-(3,3-dimethyl-cyclohexyl)-ethoxy]-2-methyl-propyl ester | Fruity, musk seeds Musk, radiant, soft, flowery aspects |
| 2 | 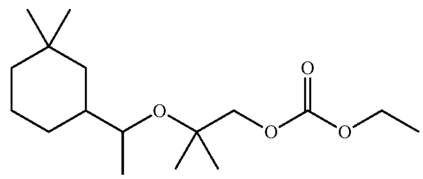 [SMILES: CCOC(=O)OCC(C)(C)OC(C)C1CCCC(C)(C)C1] | Ethyl carbonic acid-2-[1-(3,3-dimethyl-cyclohexyl)-ethoxy]-2-methyl-propyl ester | Musk seeds Musk, radiant, soft, flowery aspects |
| 3 | 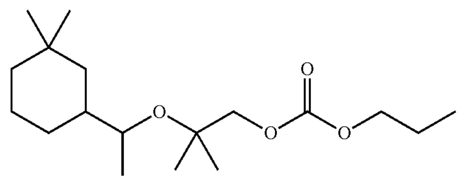 [SMILES: CCCOC(=O)OCC(C)(C)OC(C)C1CCCC(C)(C)C1] | Propyl carbonic acid-2-[1-(3,3-dimethyl-cyclohexyl)-ethoxy]-2-methyl-propyl ester | Musk, radiant, powdery-sweet, flowery aspects |
| 4 | 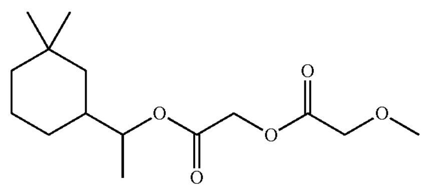 [SMILES: COCC(=O)OCC(=O)OC(C)C1CCCC(C)(C)C1] | Methoxyacetic acid-1-(3,3-dimethyl-cyclohexyl)-ethoxycarbonyl-methyl ester | Fruity, Musk, radiant, soft, flowery aspects |
| 5 | 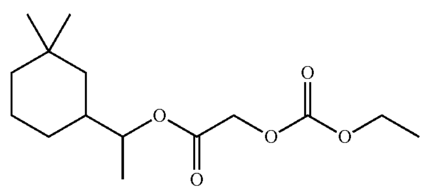 [SMILES: CCOC(=O)OCC(=O)OC(C)C1CCCC(C)(C)C1] | Ethyl carbonic acid-1-(3,3-dimethyl-cyclohexyl)-ethoxycarbonylmethyl ester | Musk seeds Musk, radiant, soft, flowery aspects |
| 6 | 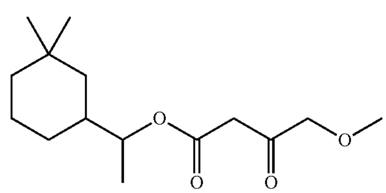 [SMILES: COCC(=O)CC(=O)OC(C)C1CCCC(C)(C)C1] | 4-Methoxy-3-oxo-butyric acid-1-(3,3-dimethyl-cyclohexyl) ethyl ester | Musk, radiant, powdery-sweet, balsam-like, flowery aspects |
| 7 | 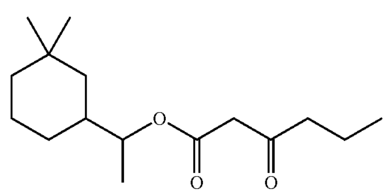 [SMILES: CCCC(=O)CC(=O)OC(C)C1CCCC(C)(C)C1] | 3-oxo-Hexanoic acid-1-(3,3-dimethyl-cyclohexyl)-ethyl ester | Musk seeds Musk, radiant, powdery-sweet, balsam-like, flowery aspects |

As well as the odor notes and olfactory properties described above, musk-like, flowery and radiant, the especially preferred compounds possess in particular the further odor notes/olfactory properties mentioned in Table 1.

The compounds according to the invention can be in optically active form and even in isomerically pure form. They can, however, also be used as any mixture of the stereoisomers, in particular also as racemates.

The compounds of the following formulae (I), (II), (V), (VI), (VIII) and (IX) are especially preferred according to the invention. These compounds possess a particularly balanced pattern of properties. Inspite of the above, in some cases according to the invention the compound methoxyacetic acid-2-[1-(3,3-dimethyl-cyclohexyl)-ethoxy]-2-methyl-propyl ester (see structure (1) hereinbelow) may not be preferred.

Furthermore, it should be pointed out that, surprisingly, with respect to their musk note, the compounds according to the invention are strongly reminiscent of musk seed oil. This can be regarded as especially valuable in many perfumery applications.

The compounds according to the invention can be produced by reactions and methods that are known per se. For example, the alcohol, formula III (specifications based on EP 04772966) can be reacted with methoxyacetic acid methyl ester or with ethyl chloroformate to the ester of formula I and II (see formula scheme).

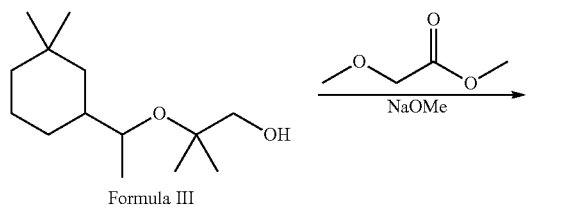

Furthermore, the compound of formula IV (specification based on EP1047660) can be reacted with methoxyacetic acid chloride or with ethyl chloroformate to the esters of formulae V and VI (see formula scheme).

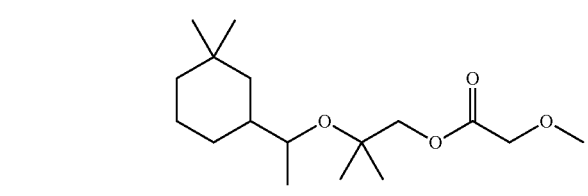

Furthermore, the compound of formula VII (Cyclademol) can be reacted with methoxyacetoacetic acid methyl ester or 3-oxo-hexanoic acid methyl ester to the esters of formulae VIII and IX (see formula scheme).

The invention also relates to a perfume mixture, preferably a perfume oil, comprising a compound according to the invention or a mixture of compounds according to the invention and one, 2, 3, 4, 5, 6, 7, 8, 9, 10 or more further perfumes, wherein the amount of the compound according to the invention or of the compounds according to the invention is sufficient to impart a flowery note to the perfume mixture or to intensify this note and to impart the odor impression radiant or to intensify this.

In the sense of the present text, "further" perfumes are perfumes other than the perfumes according to formula (A).

"Impart" a note or an odor impression is to be understood as follows, in the sense of this application:

A perfume mixture does not possess the note to be imparted or an odor impression to be imparted. Following addition of a sufficient amount of the compound according to the invention or of a mixture of the compounds according to the invention, the corresponding notes (the corresponding odor impression) are sensorially perceptible. In this case an imparting is present.

"Intensify" is to be understood as follows:

The comparative mixture V already possesses a corresponding note/a corresponding odor impression. On adding the compound according to the invention or a mixture of compounds according to the invention in a sufficient amount, the corresponding odor impression/the corresponding odor note is sensorially perceptibly intensified.

In case of doubt, the presence of imparting and/or intensifying is to be established by a panel of experts with sensory training. Intensification or imparting of an impression is present when a corresponding effect is established sensorially, reproducibly by at least 75% of the panellists.

The special properties of the compounds according to the invention can—as already mentioned—be exploited particularly well in order to produce interesting and desirable fragrance notes/properties in perfume mixtures according to the invention.

The compounds according to the invention are usually employed in sensorially effective amounts. In perfume mixtures, the compounds according to the invention are mixed with further perfumes. These further perfumes can in principle be any known perfumes.

A perfume mixture according to the invention is preferred in which the mass ratio of the total of the perfumes according to the invention to the total of the further perfumes contained in the perfume mixture is 1:1000 to 1:05, preferably 1:25 to 1:100.

At this ratio, the advantages of the compounds according to the invention can be exploited particularly well.

A perfume mixture according to the invention in which the proportion of the total of the perfumes according to the invention is 0.00001 to 99.9 wt. %, preferably 0.001 to 70 wt. % and especially preferably 0.01 to 50 wt. %, relative to the total weight of the perfume mixture, is further preferred according to the invention.

The combination of compounds according to the invention with woody perfumes (especially sandalwood and ambergris) and/or flowery perfumes is particularly suitable.

Woody perfumes that are particularly suitable for the combination are: Sandranol (2-ethyl-4-(2,2,3)-trimethylcyclopent-3-yl-but-2-en-1-ol), Ysamber K (1',1',5',5'-tetramethyl-hexahydro-spiro[1,3-dioxolane-2,8'(5'H)-2H-2,4a-methanonaphthalene]), Timberol (1-(2,2,6-trimethylcyclohexyl)hexan-3-ol), Iso-E-Super, (2,3,8,8-tetramethyl-1,2,3,4,5,6,8-octahydro-2-naphthalenyl-methyl ketone), isobornyl acetate (2-exo-bornanyl acetate) and Ylanate (2-tert-butylcyclohexyl acetate).

Flowery perfumes particularly suitable for the combination are: Lilial (2-methyl-3-(4-tert-butylphenyl)propanal), Hedion (methyl (3-oxo-2-pentyl-cyclopentyl)acetate), Mayol (4-isopropyl-cyclohexyl) methanol), linalool (3,7-dimethyl-1,6-octadien-3-ol), dihydromyrcenol (2,6-dimethyl-7-octen-2-ol), citronellol (3,7-dimethyl-6-octen-1-ol), phenoxanol (3-methyl-5-phenyl-pentanol), 2-phenylethyl alcohol, hydroxycitronellal (3,7-dimethyl-7-hydroxyoctan-1-al) and alpha-Jonon (4-(2,6,6-trimethyl-cyclohex-2-enyl)-but-3-en-2-one).

The combination of compounds according to the invention with the aforementioned woody perfumes leads to brighter, radiant and cleaner odor impressions. The mixtures have a fresher and more natural effect.

The effect on combination with flowery perfumes is in the direction of freshness and radiance. Furthermore, the flowery aspects are more rounded. The mixtures have a more intense and more harmonious odor.

Moreover, combination of the compounds according to the invention with green-fruity perfumes is often especially preferable. Suitable green-fruity perfumes are for example: Vertral (octahydro-1H-4,7-methanoindene-5-carbaldehyde), cis-3-hexen-1-ol, beta-Damascon (1-(2,6,6-trimethyl-cyclohex-2-enyl)-buten-1-one), Vertocitral (2,4-dimethylcyclohex-3-en-1-carbaldehyde), Cyclogalbanate Allyl (cyclohexyl oxyacetate) and hexyl acetate.

Combination with the aforementioned perfumes leads to a rounder and softer odor. Moreover, addition of the esters according to the invention lends a certain sparkle and imparts an impression of natural radiance.

Moreover, combination with spicy-balsamic perfumes is often preferable. Suitable spicy-balsamic perfumes are in particular: eugenol (2-methoxy-4-allylphenol), coumarin (2H-1-benzopyran-2-one), anisaldehyde (4-methoxybenzaldehyde), amyl cinnamaldehyde (2-phenyl-3-phenyl-2-propenal), isoamyl salicylate (salicylic acid-3-methylbutyl ester) and cinnamyl alcohol (3-phenyl-2-propen-1-ol).

On combining compounds according to the invention with the stated perfumes, aspects of freshness and naturalness can be observed. The action of the mixtures is more harmonious and more radiant.

In mixtures with other perfumes, the compounds according to the invention are able, even at low dosages, to intensify the intensity of a perfume mixture and to round off and harmonize the overall picture of the perfume mixture in olfactory terms and to lend the mixture more radiance and naturalness.

The invention also relates to a perfumed article comprising a compound according to the invention or a perfume mixture according to the invention, in each case in a sensorially effective amount. Moreover, it is preferable for the amount of compounds according to the invention or perfume oil according to the invention to be sufficient to impart or to intensify one or more of the odor notes radiant, musk-like, uplifting, soft, woody.

A perfumed article according to the invention is further preferred according to the invention in which in addition one, two, three or more further perfumes are contained, wherein the further perfume or perfumes preferably impart a woody and/or flowery odor.

Regarding the combination with especially preferred perfumes with woody and/or flowery odor notes, reference should be made to the account presented above.

The preferred embodiments of the invention described above with a view to uses of the compounds and perfume mixtures according to the invention also apply correspondingly to perfumed articles according to the invention, in particular the information regarding preferred proportions by weight.

By combining the compounds according to the invention with one, two, three or several perfumes (preferably with woody and/or flowery odor), new perfume compositions can be formed and/or perfumed articles with interesting odor notes can be produced. In this way particularly interesting and natural novel and original fragrance notes can be created.

Perfumes that are advantageously suitable for combination are given, for example, in S. Arctander, Perfume and Flavor Materials, Vol. I and II, Montclair, N.J. 1969, self-published, or K. Bauer et al., Common Fragrance and Flavor Materials, 4th Edition, Wiley-VCH, Weinheim 2001. In detail, we may mention:

Extracts from natural raw materials such as essential oils, concretes, absolutes, resins, resinoids, balsams, tinctures e.g. ambergris tincture; amyris oil; angelica seed oil; angelica root oil; anise oil; valerian oil; basil oil; tree moss absolute; bay oil; mugwort oil; benzoin resin; bergamot oil; beeswax absolute; birch tar oil; bitter almond oil; savory oil; bucho leaf oil; cabreuva oil; cade oil; calamus oil; camphor oil; cananga oil; cardamom oil; cascarilla oil; cassia oil; cassia absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill oil; dill seed oil; eau de brouts absolute; oak moss absolute; elemi oil; tarragon oil; eucalyptus-citriodora oil; eucalyptus oil; fennel oil; fir-needle oil; galbanum oil; galbanum resin; geranium oil; grapefruit oil; guaiac wood oil; gurjun balsam; gurjun balsam oil; helichrysum absolute; helichrysum oil; ginger oil; iris root absolute; iris root oil; jasmine absolute; calamus oil; chamomile oil blue; chamomile oil Roman; carrot seed oil; cascarilla oil; pine-needle oil; spearmint oil; caraway oil; labdanum oil; labdanum absolute; labdanum resin; lavandin absolute; lavandin oil; lavender absolute; lavender oil; lemongrass oil; lovage oil; lime oil distilled; lime oil pressed; linalool oil; litsea-cubeba oil; bay leaf oil; mace oil; marjoram oil; mandarin oil; massoy bark oil; mimosa absolute; musk seed oil; musk tincture; muscatel-sage oil; nutmeg oil; myrrh absolute; myrrh oil; myrtle oil; clove leaf oil; clove blossom oil; neroli oil; olibanum absolute; olibanum oil; opopanax oil; orange blossom absolute; orange oil; origanum oil; palmarosa oil; patchouli oil; perilla oil; Peru balsam oil; parsley leaf oil; parsley seed oil; petitgrain oil; peppermint oil; pepper oil; pimento oil; pine oil; poley oil; rose absolute; rosewood oil; rose oil; rosemary oil; Dalmatian sage oil; Spanish sage oil; sandalwood oil; celery seed oil; spike lavender oil; star anise oil; styrax oil; tagetes oil; fir-needle oil; tea tree oil; turpentine oil; thyme oil; tolu balsam; tonka absolute; tuberose absolute; vanilla extract; violet leaf absolute; verbena oil; vetiver oil; juniper berry oil; wine lees oil; wormwood oil; wintergreen oil; ylang-ylang oil; hyssop oil; civet absolute; cinnamon leaf oil; cinnamon bark oil and fractions thereof, or ingredients isolated therefrom;

Individual perfumes from the group of the hydrocarbons, e.g. 3-carene; α-pinene; β-pinene; α-terpinene; γ-terpinene; ρ-cymene; bisabolene; camphene; caryophyllene; cedrene; farnesene; limonene; longifolene; myrcene; ocimene; valencene; (E,Z)-1,3,5-undecatriene; styrene; diphenylmethane;

of the aliphatic alcohols e.g. hexanol; octanol; 3-octanol; 2,6-dimethyl heptanol; 2-methyl-2-heptanol; 2-methyl-2-octanol; (E)-2-hexenol; 1-octen-3-ol; mixture of 3,4,5,6,6-pentamethyl-3/4-hepten-2-ol and 3,5,6,6-tetramethyl-4-methylene heptan-2-ol; (E,Z)-2,6-nonadienol; 3,7-dimethyl-7-methoxyoctan-2-ol; 9-decenol; 10-undecenol; 4-methyl-3-decen-5-ol;

of the aliphatic aldehydes and acetals thereof e.g. hexanal; heptanal; octanal; nonanal; decanal; undecanal; dodecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanaldiethylacetal; 1,1-dimethoxy-2,2,5-trimethyl-4-hexene; citronellyloxy acetaldehyde; 1-(1-methoxy-propoxy)-(E/Z)-3-hexene;

of the aliphatic ketones and oximes thereof e.g. 2-heptanone; 2-octanone; 3-octanone; 2-nonanone; 5-methyl-3-heptanone; 5-methyl-3-heptanone-oxime; 2,4,4,7-tetramethyl-6-octen-3-one; 6-methyl-5-hepten-2-one;

of the aliphatic sulfur-containing compounds e.g. 3-methylthio-hexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

of the aliphatic nitriles e.g. 2-nonenoic acid nitrile; 2-undecenoic acid nitrile; 2-tridecenoic acid nitrile; 3,12-tridecadienoic acid nitrile; 3,7-dimethyl-2,6-octadienoic acid nitrile; 3,7-dimethyl-6-octenoic acid nitrile;

of the esters of aliphatic carboxylic acids e.g. (E)- and (Z)-3-hexenylformate; ethyl acetoacetate; isoamyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl-isobutyrate; hexylcrotonate; ethyl isovalerate; ethyl-2-methylpentanoate; ethyl hexanoate; allyl hexanoate; ethyl heptanoate; allyl heptanoate; ethyl octanoate; ethyl-(E,Z)-2,4-decadienoate; methyl-2-octinate; methyl-2-noninate; allyl-2-isoamyloxyacetate; methyl-3,7-dimethyl-2,6-octadienoate; 4-methyl-2-pentyl-crotonate;

of the acyclic terpene alcohols e.g. geraniol; nerol; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and formates, acetates, propionates, isobutyrates, butyrates, isovalerates, pentanoates, hexanoates, crotonates, tiglinates and 3-methyl-2-butenoates thereof;

of the acyclic terpene aldehydes and ketones e.g. citronellal; 7-methoxy-3,7-dimethyloctanal; 2,6,10-trimethyl-9-undecenal; geranyl acetone; and the dimethyl and diethyl acetals of geranial, neral, of the cyclic terpene alcohols e.g. menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiol; and formates, acetates, propionates, isobutyrates, butyrates, isovalerates, pentanoates, hexanoates, crotonates, tiglinates and 3-methyl-2-butenoates thereof;

of the cyclic terpene aldehydes and ketones e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethyl-ionone; alpha-irone; beta-damascenone; 1-(2,4,4-trimethyl-2-cyclohexen-1-yl)-2-buten-1-one; 1,3,4,6,7,8a-hexahydro-1,1,5,5-tetramethyl-2H-2,4a-methano-naphthalen-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedar wood oil (methylcedryl ketone);

of the cyclic alcohols e.g. 4-tert.-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

of the cycloaliphatic alcohols e.g. alpha,3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl) pentan-3-ol; 1-(2,2,6-trimethylcyclohexyl) hexan-3-ol;

of the cyclic and cycloaliphatic ethers e.g. cineol; cedrylmethyl ether; cyclododecylmethyl ether; 1,1-dimethoxycyclododecane; (ethoxymethoxy)cyclo-dodecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

of the cyclic and macrocyclic ketones e.g. 4-tert.-butylcyclohexanone; 2,2,5-trimethyl-5-pentylcyclopentanone; 2-heptylcyclopentanone; 2-pentyl-cyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4 (5H)-indanone; 8-cyclohexadecen-1-one; 9-cycloheptadecen-1-one; cyclopentadecanone; cyclohexadecanone;

of the cycloaliphatic aldehydes e.g. 2-methyl-4-(2,2,6-trimethyl-cyclohexen-1-yl)-2-butenal; 4-(4-hydroxy-4-methylpentyl)-3-cyclohexene carbaldehyde; 4-(4-methyl-3-penten-1-yl)-3-cyclohexene carbaldehyde;

of the cycloaliphatic ketones e.g. 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenylmethyl ketone; methyl-2,6,10-trimethyl-2,5,9-cyclododecatrienyl ketone; tert.-butyl-(2,4-dimethyl-3-cyclohexen-1-yl) ketone;

of the esters of cyclic alcohols e.g. 2-tert-butylcyclohexyl acetate; 4-tert-butylcyclohexyl acetate; 2-tert-pentylcyclohexyl acetate; 4-tert-pentyl-cyclohexyl acetate; 3,3,5-trimethylcyclohexyl acetate; decahydro-2-naphthyl acetate; 2-cyclo-pentylcyclopentylcrotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5, or 6-indenyl acetate; 4,7-methano-3a,4,5,6,7,7a-hexahydro-5, or 6-indenyl-propionate; 4,7-methano-3a,4,5,6,7,7a-hexahydro-5, or 6-indenyl isobutyrate; 4,7-methanooctahydro-5, or 6-indenyl acetate;

of the esters of cycloaliphatic alcohols e.g. 1-cyclohexylethylcrotonate;

of the esters of cycloaliphatic carboxylic acids e.g. allyl-3-cyclohexylpropionate; allylcyclohexyloxyacetate; cis- and trans-methyldihydrojasmonate; cis- and trans-methyljasmonate; methyl-2-hexyl-3-oxocyclopentane carboxylate; ethyl-2-ethyl-6,6-dimethyl-2-cyclohexene carboxylate; ethyl-2,3,6,6-tetramethyl-2-cyclohexene carboxylate; ethyl-2-methyl-1,3-dioxolane-2 acetate;

of the araliphatic alcohols e.g. benzyl alcohol; 1-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenyl-propanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

of the esters of araliphatic alcohols and aliphatic carboxylic acids e.g. benzyl acetate; benzyl propionate; benzyl isobutyrate; benzyl isovalerate; 2-phenylethyl acetate; 2-phenylethylpropionate; 2-phenylethylisobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethylisobutyrate; 4-methoxybenzyl acetate;

of the araliphatic ethers e.g. 2-phenylethylmethyl ether; 2-phenylethyl-isoamyl ether; 2-phenylethyl-1-ethoxyehl ether; phenylacetaldehyde dimethylacetal; phenylacetaldehyde diethylacetal; hydratropa aldehyde dimethylacetal; phenylacetaldehyde glycerinacetal; 2,4,6-trimethyl-4-phenyl-1,3-dioxane; 4,4a,5,9b-tetra-hydroindeno[1,2-d]-m-dioxin; 4,4a,5,9b-tetrahydro-2,4-dimethylindeno[1,2-d]-m-dioxin;

of the aromatic and araliphatic aldehydes e.g. benzaldehyde; phenylacetaldehyde; 3-phenylpropanal; hydratropa aldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-isobutylphenyl)propanal; 3-(4-tert.-butyl-phenyl) propanal; cinnamaldehyde; alpha-butyl cinnamaldehyde; alpha-hexyl cinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylene dioxybenzaldehyde; 3,4-dimethoxybenzaldehyde; 2-methyl-3-(4-methoxyphenyl)propanal; 2-methyl-3-(4-methylene dioxyphenyl)propanal;

of the aromatic and araliphatic ketones e.g. acetophenone; 4-methylacetophenone; 4-methoxyacetophenone; 4-tert.-butyl-2,6-dimethylaceto-phenone; 4-phenyl-2-butanone; 4-(4-hydroxyphenyl)-2-butanone; 1-(2-naphthalenyl) ethanone; 2-benzofuranylethanone; (3-methyl-2-benzofuranyl)ethanone; benzophenone; 1,1,2,3,3,6-hexamethyl-5-indanylmethyl ketone; 6-tert.-butyl-1,1-dimethyl-4-indanylmethyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

of the aromatic and araliphatic carboxylic acids and esters thereof e.g. benzoic acid; phenylacetic acid; methyl benzoate; ethyl benzoate; hexyl benzoate; benzyl benzoate; methylphenyl acetate; ethylphenyl acetate; geranylphenyl acetate; phenylethyl-phenyl acetate; methyl cinnamate; ethyl cinnamate; benzyl cinnamate; phenylethyl cinnamate; cinnamyl cinnamate; allylphenoxyacetate; methyl salicylate; hexyl salicylate; cyclohexyl salicylate; cis-3-hexenyl salicylate; benzyl salicylate; phenylethyl salicylate; methyl-2,4-dihydroxy-3,6-dim ethyl benzoate; ethyl-3-phenylglycidate; ethyl-3-methyl-3-phenylglycidate;

of the nitrogen-containing aromatic compounds e.g. 2,4,6-trinitro-1,3-dimethyl-5-tert.-butylbenzene; 3,5-dinitro-2,6-dimethyl-4-tert.-butylacetophenone; cinnamic acid nitrile; 3-methyl-5-phenyl-2-pentenoic acid nitrile; 3-methyl-5-phenylpentanoic acid nitrile; methylanthranilate; methyl-N-methylanthranilate; Schiff's bases of methylanthranilate with 7-hydroxy-3,7-dimethyloctanal, 2-methyl-3-(4-tert.-butyl-phenyl)propanal or 2,4-dimethyl-3-cyclohexene carbaldehyde; 6-isopropylquinoline; 6-isobutylquinoline; 6-sec.-butylquinoline; 2-(3-phenylpropyl)pyridine; indole; skatole; 2-methoxy-3-isopropylpyrazine; 2-isobutyl-3-methoxypyrazine;

of the phenols, phenyl ethers and phenyl esters e.g. estragol; anethol; eugenyl methyl ether; isoeugenol; isoeugenyl methyl ether; thymol; carvacrol; diphenyl ether; betanaphthylmethyl ether; beta-naphthylethyl ether; beta-naphthyl isobutyl ether; 1,4-dimethoxybenzene; eugenyl acetate; 2-methoxy-4-methylphenol; 2-ethoxy-5-(1-propenyl)phenol; p-cresylphenyl acetate;

of the heterocyclic compounds e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

of the lactones e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,12-dodecanedioate; ethylene-1,13-tridecanedioate; 2,3-dihydrocoumarin; octahydrocoumarin.

If the compounds according to the invention or a corresponding mixture are mainly used for giving a perfume composition more rounding and/or harmony and/or to intensify particular notes, the total amount of the compounds according to the invention is preferably comparatively low and especially preferably in the range from 0.01 to 5 wt. %, more preferably in the range from 0.1 to 2 wt. %, relative to the total amount of the perfume or aromatic substance composition.

Perfume compositions according to the invention can be used for perfuming in liquid form, undiluted or diluted with a solvent. Suitable solvents for this are for example ethanol, isopropanol, diethylene glycol monoethyl ether, glycerol, propylene glycol, 1,2-butylene glycol, dipropylene glycol, diethyl phthalate, triethyl citrate, isopropyl myristate, triacetin etc.

Moreover, perfume compositions according to the invention can be absorbed on a carrier substance, which provides both fine distribution of the perfumes in the perfumed article according to the invention and controlled release during use. Said carriers can be porous inorganic materials such as light sulfate, silica gels, zeolites, gypsums, clays, clay granules, gas concrete etc. or organic materials such as wood, cellulose-based substances, sugars, dextrins (e.g. maltodextrin) or plastics such as PVC, polyvinyl acetates or polyurethanes. However, the combination of perfume mixture according to the invention and carrier substance also itself already represents an example of perfumed article according to the invention.

Perfume or aromatic substance compositions according to the invention, which contain compounds, can also be in microencapsulated or spray-dried form, as inclusion complexes or as extruded products (i.e. articles according to the invention) and in this form can for example be further processed to some other perfumed article.

Optionally, the properties of the compositions modified in this way can be further optimized by so-called "coating" with suitable materials with a view to more targeted release of fragrance, for which preferably wax-like plastics e.g. polyvinyl alcohol are used. The resultant products once again represent perfumed articles according to the invention.

The microencapsulation of the perfume compositions according to the invention to articles according to the invention can for example be carried out by the so-called coacervation method using capsule materials e.g. of polyurethane-like substances or soft gelatin. The spray-dried perfume compositions according to the invention can for example be produced by spray-drying of an emulsion or dispersion containing the perfume or aromatic substance composition, wherein modified starch, proteins, dextrin and plant gums can be used as carrier substances. Inclusion complexes can be produced for example by placing dispersions of the perfume composition and cyclodextrins or urea derivatives in a suitable solvent, e.g. water. Extruded products can be obtained by melting the perfume compositions with a suitable wax-like substance and by extrusion followed by solidification, optionally in a suitable solvent, e.g. isopropanol.

Compounds according to the invention and perfume compositions that contain compounds can be used in concentrated form, in solutions or in the modified form described above for the production of perfumed articles according to the invention, e.g. perfume extracts, eau de parfum, eau de toilette, aftershave, eau de cologne, pre-shave products, splash colognes and perfumed tissue wipes and for the perfuming of acidic, alkaline and neutral cleaning agents, e.g. floor cleaners, window glass cleaners, washing-up liquids, bath and sanitary cleaners, liquid scouring agents, solid and liquid lavatory cleaners, powder and foam carpet cleaners, textile fresheners, ironing aids, liquid detergents, powder detergents, laundry pretreatment agents such as bleach, soaking agents and stain removers, fabric softeners, washing soaps, washing tablets, disinfectants, surface disinfectants and air fresheners in liquid or gel form or applied on a solid carrier, aerosol sprays, waxes and polishes such as furniture polish, floor polish, shoe creams and body care products e.g. solid and liquid soaps, shower gels, shampoos, shaving soaps, shaving foams, bath oils, cosmetic emulsions of the oil-in-water, water-in-oil and water-in-oil-in-water type e.g. skin creams and lotions, face creams and lotions, sunscreen creams and lotions, after-sun creams and lotions, hand creams and lotions, foot creams and lotions, depilatory creams and lotions, after-shave creams and lotions, tanning creams and lotions, hair care products e.g. hair sprays, hair gels, fixing hair lotions, hair rinses, permanent and semi-permanent hair colorants, hair shaping agents such as cold waves and hair-straightening agents, hair lotions, hair creams and lotions, deodorants and antiperspirants e.g. underarm sprays, roll-ons, stick deodorants, cream deodorants, products of decorative cosmetics e.g. eye shadow, nail varnishes, make-up, lipsticks, mascara and of candles, lamp oils, joss sticks, insecticides, repellents and propellants.

The compounds according to the invention or the corresponding perfume mixtures according to the invention can be incorporated in scented articles or articles that are to be scented, in particular preparations used in nutrition, in oral hygiene or for pleasure.

Preparations used for nutrition or for pleasure are e.g. baked products (e.g. bread, biscuits, cakes, other baked goods), confectionery (e.g. chocolates, chocolate bar products, other bar products, fruit gums, hard-boiled sweets, toffees, chewing gum), alcoholic or non-alcoholic beverages (e.g. coffee, tea, wine, wine-containing beverages, beer, beer-containing beverages, liqueurs, spirits, brandies, fruit-containing lemonades, isotonic beverages, refreshing beverages, nectars, fruit and vegetable juices, fruit or vegetable juice preparations), instant beverages (e.g. instant-cocoa beverages, instant-tea beverages, instant-coffee beverages), meat products (e.g. ham, sausage or raw-sausage preparations, spiced or marinated fresh or salted meat products), eggs or egg products (egg powder, egg white, yolk), cereal products (e.g. breakfast cereals, muesli bars, precooked finished rice products), milk products (e.g. milk beverages, milk ices, yoghurt, kefir, fresh cheese, soft cheese, hard cheese, dried milk powder, whey, butter, buttermilk, partially or fully hydrolyzed lactoprotein-containing products), products from soya protein or other soya bean fractions (e.g. soya milk and products prepared therefrom, preparations containing soya lecithin, fermented products such as tofu or tempeh or products prepared therefrom, soya sauces), fruit preparations (e.g.

jams, fruit ices, fruit sauces, fruit fillings), vegetable preparations (e.g. ketchup, sauces, dried vegetables, deep-frozen vegetables, precooked vegetables, vegetables pickled in vinegar, preserved vegetables), "nibbles" (e.g. roasted or fried potato chips or potato dough products, bread dough products, extruded products based on maize or peanut), products based on fats and oils or emulsions thereof (e.g. mayonnaise, remoulade, dressings, spiced preparations), other ready-meals and soups (e.g. dry soups, instant soups, precooked soups), spices, flavoring mixtures and especially seasonings, which for example find application for snacks. After incorporating the compounds according to the invention or the corresponding mixtures, these preparations are preparations according to the invention (as an example of articles according to the invention).

Preparations according to the invention can for example be in the form of semi-finished goods or as a flavoring mixture.

Preparations according to the invention can serve in particular as semi-finished goods for the production of further preparations used for nutrition or for pleasure, in particular in spray-dried form. Preparations according to the invention can also be in the form of capsules, tablets (plain and coated tablets, e.g. enteric coatings), sugar-coated tablets, granules, pellets, solid mixtures, dispersions in liquid phases, as emulsions, as powders, as solutions, as pastes or as other preparations for swallowing or chewing as food supplements.

Preparations according to the invention used for oral hygiene are in particular mouth and/or dental hygiene agents such as toothpastes, tooth gels, tooth powders, mouthwashes, chewing gums and other oral hygiene products.

Other usual active ingredients, basic ingredients, auxiliary ingredients and additives for preparations according to the invention used for nutrition, for oral hygiene or for pleasure can be contained in amounts from 5 to 99.999999 wt. %, preferably 10 to 80 wt. %, relative to the total weight of the preparation. In addition the preparations can have water in an amount up to 99.999999 wt. %, preferably 5 to 80 wt. %, relative to the total weight of the preparation.

Preparations according to the invention (as examples of perfumed articles according to the invention), containing compounds, are produced, according to a preferred embodiment, by incorporating the compounds according to the invention as substance, as solution (e.g. in ethanol, water or 1,2-propylene glycol) or in the form of a mixture with a solid or liquid carrier substance (e.g. maltodextrin, starch, silica gel), other flavorings or aromatic substances and optionally further aids and/or stabilizers (e.g. natural or artificial polysaccharides and/or plant gums such as modified starches or gum arabic) in a basis-preparation serving for nutrition, for oral hygiene or for pleasure. Advantageously, fragrance mixtures according to the invention in the form of solution and/or suspension or emulsion can also be converted by spray-drying into a solid preparation according to the invention (semi-finished product).

The spray-dried solid preparations according to the invention (as example of article according to the invention) are particularly suitable as semi-finished products for the production of further preparations according to the invention. The spray-dried solid preparations according to the invention preferably contain 50 to 95 wt. % carrier substances, in particular maltodextrin and/or starch, 5 to 40% excipients, preferably natural or artificial polysaccharides and/or plant gums such as modified starches or gum arabic.

According to another preferred embodiment, for the production of preparations according to the invention, compounds and optionally other constituents of the preparation according to the invention are first incorporated in emulsions, in liposomes, e.g. starting from phosphatidyl choline, in microspheres, in nanospheres or also in capsules, granules or extrudates from a matrix suitable for foodstuffs and luxuries, e.g. from starch, starch derivatives (e.g. modified starch), cellulose or cellulose derivatives (e.g. hydroxypropylcellulose), other polysaccharides (e.g. dextrin, alginate, curdlan, carrageenan, chitin, chitosan, pullulan), natural fats, natural waxes (e.g. beeswax, carnauba wax), from proteins, e.g. gelatin or other natural products (e.g. shellac). Depending on the matrix, the products can be obtained by spray-drying, spray-granulation, melt-granulation, coacervation, coagulation, extrusion, melt-extrusion, emulsification, coating or other suitable encapsulation methods and optionally a suitable combination of the aforementioned methods. In another preferred method of production for a preparation according to the invention, compounds are first complexed with one or more complexing agents, for example with cyclodextrins or cyclodextrin derivatives, preferably α- or β-cyclodextrin, and used in this complexed form.

A preparation according to the invention is especially preferred in which the matrix is selected so as to provide delayed release of the compounds according to the invention from the matrix, so that a long-lasting action is achieved. In this respect, a fat, wax, polysaccharide or protein matrix is especially preferred.

As further constituents for preparations according to the invention, used for nutrition or for pleasure, it is possible for the usual basic substances, auxiliary substances and additives for foodstuffs or luxuries to be used, e.g. water, mixtures of fresh or processed plant or animal basic materials or raw materials (e.g. raw, baked, dried, fermented, smoked and/or boiled meat, bone, cartilage, fish, vegetables, fruit, herbs, nuts, vegetable or fruit juices or pastes or mixtures thereof), digestible or indigestible carbohydrates (e.g. sucrose, maltose, fructose, glucose, dextrins, amylose, amylopectin, inulin, xylan, cellulose, tagatose), sugar alcohols (e.g. sorbitol, erythritol), natural or hardened fats (e.g. tallow, lard, palm fat, coconut fat, hardened plant fat), oils (e.g. sunflower oil, peanut oil, maize oil, olive oil, fish oil, soya oil, sesame oil), fatty acids or salts thereof (e.g. potassium stearate), proteinogenic or non-proteinogenic amino acids and related compounds (e.g. γ-aminobutyric acid, taurine), peptides (e.g. glutathione), native or processed proteins (e.g. gelatin), enzymes (e.g. peptidases), nucleic acids, nucleotides, taste correctants for unpleasant taste impressions, further taste modulators for further, as a rule not unpleasant taste impressions, other taste modulating substances (e.g. inositol phosphate, nucleotides such as guanosine monophosphate, adenosine monophosphate or other substances such as sodium glutamates or 2-phenoxypropionic acid), emulsifiers (e.g. lecithins, diacyl glycerols, gum arabic), stabilizers (e.g. carrageenan, alginate), preservatives (e.g. benzoic acid, sorbic acid), antioxidants (e.g. tocopherol, ascorbic acid), chelating agents (e.g. citric acid), organic or inorganic acidifiers (e.g. malic acid, acetic acid, citric acid, tartaric acid, phosphoric acid), bitter substances (e.g. quinine, caffeine, limonin, amarogentin, humulones, lupolones, catechins, tannins), mineral salts (e.g. sodium chloride, potassium chloride, magnesium chloride, sodium phosphates), the enzymatic browning inhibitors (e.g. sulfite, ascorbic acid), essential oils, plant extracts, natural or synthetic dyes or coloring pigments (e.g. carotenoid, flavonoids, anthocyans, chlorophyll and derivatives thereof), spices, trigeminally active substances or plant extracts containing said trigeminally active substances, synthetic, natural or nature-identical aromatic substances or perfumes and odor correctants.

Dentifrices (as a basis for preparations used for oral hygiene), which contain compounds, generally comprise an abrasive system (grinding or polishing agents), e.g. silicic acids, calcium carbonates, calcium phosphates, aluminum oxides and/or hydroxyapatites, surface-active substances e.g. sodium lauryl sulfate, sodium lauryl sarcosinate and/or cocamidopropylbetaine, humectants e.g. glycerol and/or sorbitol, thickeners, e.g. carboxymethylcellulose, polyethylene glycols, carrageenan and/or Laponite®, sweeteners, e.g. saccharin, taste correctants for unpleasant taste impressions, taste correctants for other, as a rule not unpleasant taste impressions, taste modulating substances (e.g. inositol phosphate, nucleotides such as guanosine monophosphate, adenosine monophosphate or other substances such as sodium glutamates or 2-phenoxypropionic acid), substances with a cooling effect e.g. menthol, menthol derivatives (e.g. L-menthol, L-menthyllactate, L-menthylalkyl carbonates, menthone ketals, menthane-carboxylic acid amides), 2,2,2-trialkylacetic acid amides (e.g. 2,2-diisopropylpropionic acid methyl amide), icilin and icilin derivatives, stabilizers and active substances, e.g. sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, cetylpyridinium chloride, aluminum lactate, potassium citrate, potassium nitrate, potassium chloride, strontium chloride, hydrogen peroxide, flavorings and/or sodium bicarbonate or odor correctants.

Chewing gums (as a further example of preparations used for oral hygiene), which contain compounds, generally comprise a chewing gum base, i.e. a chewing mass that becomes plastic during chewing, sugars of various types, sugar substitutes, other sweet-tasting substances, sugar alcohols, taste correctants for unpleasant taste impressions, other taste modulators for further, as a rule not unpleasant taste impressions, taste modulating substances (e.g. inositol phosphate, nucleotides such as guanosine monophosphate, adenosine monophosphate or other substances such as sodium glutamates or 2-phenoxypropionic acid), humectants, thickeners, emulsifiers, flavorings and stabilizers or odor correctants.

Preferably, the preparations according to the invention can also contain, in addition to the compounds according to the invention, a flavoring composition, in order to round off and refine the taste and/or odor of the preparation. Suitable (additional) flavoring compositions contain e.g. synthetic, natural or nature-identical aromatic substances, perfumes and flavorings and suitable auxiliary and carrier substances.

The invention also relates to the use of a compound according to the invention for imparting or intensifying the odor note musk-like in combination with imparting or intensifying the odor note flowery while simultaneously imparting or intensifying the odor impression radiant.

The fact that the compounds according to the invention can impart the aforementioned three aspects simultaneously makes them particularly valuable in perfumery. This is—as already mentioned—a surprising aspect of the present invention.

The invention also relates to the use of a compound according to the invention for imparting or intensifying one or more odor notes selected from the group woody, green-fruity and spicy-balsamic and/or for imparting or intensifying one or more odor impressions selected from the group consisting of bright, uplifting, soft, fresh, natural and harmonious.

The compounds according to the invention and the perfume mixture according to the invention and optionally products according to the invention are also suitable for providing (a) hair, (b) skin or (c) textile fibers with an, in particular, musk-like fragrance (regarding other odor or taste notes, see above). The present invention also relates to corresponding processes and (preferably surfactant-containing) mixtures.

According to a related aspect, the present invention also relates to the use of the compounds according to the invention as a means for increasing the substantivity and/or retention of a perfume mixture and/or as fixative and/or as a means for increasing the odor of other perfumes, perceived via a surfactant-containing aqueous solution.

Furthermore, the compounds according to the invention are suitable not only for intensifying the aforementioned special perfumes, but they are also able to form a basis, in corresponding mixtures, as so-called booster (intensifier, enhancer).

As already mentioned, besides their primary, olfactory properties, the compounds according to the invention additionally possess positive secondary properties, e.g. high stability under particular conditions of use, high yield and good adherence and high substantivity, so that they are suitable for uses where these additional properties are important.

The compounds according to the invention, or the mixtures containing such compounds, can preferably be used in order to lend a perfume composition rounding and/or harmony and/or to intensify odor notes that are present.

The invention also relates to a method of producing a perfume mixture or a perfumed product comprising the steps:
a) providing a compound according to the invention or a mixture of compounds according to the invention,
b) providing the further constituents of the perfume mixture or of the perfumed product and
c) bringing the constituents from step b) in contact with a sufficient amount of the constituent or constituents from step a) for the sensorially effective imparting or intensifying of the odor note musk-like in combination with imparting or intensifying the odor note flowery while simultaneously imparting or intensifying the odor impression radiant.

With this method according to the invention it is possible to exploit the special properties of the compounds according to the invention. For this, the constituents b) and a) are often brought in contact by mixing. However, for example in the case of solid products, spraying is also conceivable.

In this connection, a person skilled in the art is aware that for the sensorially effective imparting or intensifying of the odor notes and odor impressions, it is not only the total concentration of the compounds according to the invention that is important, but also the manner of bringing in contact. Thus, it is for example conceivable that—especially in the case of larger perfumed—on parts of the surface there is a high enough concentration, so that sensory effectiveness is provided.

Moreover, it should also be pointed out that the advantages and preferred embodiments described for the products according to the invention can of course also be transferred appropriately to the methods and uses according to the invention, and vice versa. The invention is explained in more detail below, on the basis of examples. Unless stated otherwise, the information given refers to weight.

EXAMPLE 1

Preparation of methoxyacetic acid-2-[1-(3,3-dimethyl-cyclohexyl)-ethoxy]-2-methyl-propyl ester (based on the method according to EP 0472966)

57 g (0.25 mol) of 2-[1-(3,3-dimethyl-cyclohexyl)-ethoxy]-2-methyl-propan-1-ol, 41.6 g (0.4 mol) of methoxyacetic acid methyl ester and 0.3 g of sodium methylate in 50 g methanol were placed in a 250-ml stirred vessel and were boiled under reflux. During this, methanol was distilled off via a still head. Then 100 ml water and 100 ml toluene were added to the reaction solution at room temperature, the aqueous phase was separated, the organic phase was washed with water until neutral and concentrated by evaporation. The raw product (81 g) was fractionated on a 30-cm Vigreux column in vacuum.

Yield: 60.7 g (80.9% of theoretical) B.p.: 135°-140° C./2 mbar

GC evaluation (20 m ZB-WAX, inside diameter 0.18 μm/60-9-220° C. cold feed system)

EXAMPLE 2

Preparation of Ethyl Carbonic Acid-2-[1-(3,3-dimethyl-cyclohexyl)-ethoxy]-2-methyl-propyl ester (Based on the Method According to EPO472966)

57 g (0.25 mol) of 2-[1-(3,3-dimethyl-cyclohexyl)-ethoxy]-2-methyl-propan-1-ol, 47.2 g (0.4 mol) of diethyl carbonate and 1 g of zirconium n-propylate 70% were placed in a 250-ml stirred vessel and, up to an internal temperature of 140° C., ethanol was distilled off via a still head. Then 100 ml water and 100 ml toluene were added to the reaction solution at room temperature, the aqueous phase was separated, the organic phase was washed with water until neutral and concentrated by evaporation. The raw product (81 g) was fractionated on a 30-cm Vigreux column in vacuum.

Yield: 61.5 g (82% of theoretical) B.p.: 135°-140° C./2 mbar

GC evaluation (20 m ZB-WAX, inside diameter 0.18 μm/60-9-220° C. cold feed system)

EXAMPLE 3

Preparation of methoxyacetic acid-1-(3,3-dimethyl-cyclohexyl)-ethoxycarbonylmethyl ester (based on the method according to EP1047660)

53.5 g (0.25 mol) of hydroxyacetic acid-1-(3,3-dimethyl-cyclohexyl)-ethyl ester and 25.7 g (0.325 mol) of pyridine in 100 ml MTBE were placed in a 500-ml stirred vessel. Then 28.1 g (0.26 mol) of methoxyacetic acid chloride was added dropwise at room temperature, with cooling. Then 100 ml water and 100 ml toluene were added to the reaction solution at room temperature, the aqueous phase was separated, the organic phase was washed with dilute sulfuric acid, soda solution and water until neutral and concentrated by evaporation. The raw product (73 g) was fractionated on a 30-cm Vigreux column in vacuum.

Yield: 61.4 g (85.9% of theoretical) B.p.: 135°-140° C./0.4 mbar

GC evaluation (20 m ZB-WAX, inside diameter 0.18 μm/60-9-220° C. cold feed system)

EXAMPLE 4

Preparation of ethyl carbonic acid-1-(3,3-dimethyl-cyclohexyl)-ethoxy-carbonylmethyl ester (based on the method according to EP1047660)

53.5 g (0.25 mol) of hydroxyacetic acid-1-(3,3-dimethyl-cyclohexyl)-ethyl ester and 25.7 g (0.325 mol) of pyridine in 100 ml MTBE were placed in a 500-ml stirred vessel. Then 28.1 g (0.26 mol) of ethyl chloroformate was added dropwise at room temperature, with cooling. Then 100 ml water and 100 ml MTBE were added to the reaction solution at room temperature, the aqueous phase was separated, the organic phase was washed with dilute sulfuric acid, soda solution and water until neutral and concentrated by evaporation. The raw product (73 g) was fractionated on a 30-cm Vigreux column in vacuum.

Yield: 60.4 g (84.5% of theoretical) B.p.: 135°-140° C./0.4 mbar

GC evaluation (20 m ZB-WAX, inside diameter 0.18 μm/60-9-220° C. cold feed system)

EXAMPLE 5

Preparation of 4-methoxy-3-oxo-butyric acid-1-(3,3-dimethylcyclohexyl)-ethyl ester (based on the method according to EP 1398366)

78 g (0.5 mol) of 1-(3,3-dimethyl-cyclohexyl)-ethanol, 80.3 g (0.55 mol) of 4-methoxy-3-oxo-butanecarboxylic acid methyl ester and 0.6 g sodium ethylate in 50 g methanol were placed in a 500-ml stirred vessel and boiled under reflux, distilling-off the methanol via a still head. Then 100 ml water and 100 ml toluene were added to the reaction solution at room temperature, the aqueous phase was separated, the organic phase was washed with water until neutral and concentrated by evaporation. The raw product (136 g) was fractionated on a 30-cm Vigreux column in vacuum.

Yield: 107.5 g (79.6% of theoretical) B.p.: 135°-140° C./0.4 mbar

GC evaluation (20 m ZB-WAX, inside diameter 0.18 μm/60-9-220° C. cold feed system)

EXAMPLE 6

Preparation of 3-oxo-hexanoic acid-1-(3,3-dimethyl-cyclohexyl)-ethyl ester (based on the method according to EP 1398366)

78 g (0.5 mol) of 1-(3,3-dimethyl-cyclohexyl)-ethanol, 86.9 g (0.55 mol) of 3-oxo-hexanecarboxylic acid ethyl ester and 0.6 g sodium ethylate in 50 g ethanol were placed in a 500-ml stirred vessel and boiled under reflux, distilling-off the ethanol via a still head. Then 100 ml water and 100 ml toluene were added to the reaction solution at room temperature, the aqueous phase was separated, the organic phase was washed with water until neutral and concentrated by evaporation. The raw product (139 g) was fractionated on a 30-cm Vigreux column in vacuum.

Yield: 105.9 g (79% of theoretical) B.p.: 135°-140° C./0.5 mbar

GC evaluation (20 m ZB-WAX, inside diameter 0.18 μm/60-9-220° C. cold feed system)

The spectroscopic data of the esters prepared were determined. The data are presented below.

GC/MS Data of the Esters

1. Methoxyacetic acid-2-[1-(3,3-dimethyl-cyclohexyl)-ethoxy]-2-methylpropyl ester MS: m/z (%)=139 (46), 117 (19), 97 (15), 83 (64), 73 (100), 69 (45), 57 (22), 55 (50), 43 (21), 41 (32).

2. Ethyl carbonic acid-2-[1-(3,3-dimethyl-cyclohexyl)-ethoxy]-2-methylpropyl ester MS: m/z (%)=145 (97), 139 (42), 83 (54), 73 (100), 69 (43), 57 (23), 55 (69), 43 (24), 41 (38), 29 (36).

3. Methoxyacetic acid-1-(3,3-dimethyl-cyclohexyl)-ethoxycarbonylmethyl ester

MS: m/z (%)=138 (47), 123 (85), 109 (58), 95 (55), 83 (69), 81 (46), 69 (100), 55 (56), 45 (97), 41 (43).

4. Ethyl carbonic acid-1-(3,3-dimethyl-cyclohexyl)-ethoxycarbonylmethyl ester

MS: m/z (%)=123 (85), 109 (67), 95 (59), 83 (80), 82 (45), 81 (47), 69 (100), 55 (55), 41 (49), 29 (41).

5. 4-Methoxy-3-oxo-butyric acid-1-(3,3-dimethylcyclohexyl)-ethyl ester

MS: m/z (%)=132 (60), 123 (41), 115 (38), 114 (11), 83 (92), 81 (37), 69 (92), 57 (32), 55 (60), 45 (100), 41 (47).

6. 3-oxo-Hexanoic acid-1-(3,3-dimethyl-cyclohexyl)-ethyl ester

MS: m/z (%)=138 (50), 123 (69), 109 (62), 95 (54), 83 (55), 71 (100), 69 (83), 55 (45), 43 (67), 41 (51).

EXAMPLE 7

Perfume Composition

| Constituent | wt.-‰ |
|---|---|
| Agrumex LC | 10.00 |
| Amarocit ® 10% in DPG | 10.00 |
| Ambroxide cryst. | 10.00 |
| Basil oil | 10.00 |
| Calone 1951 10% in DPG | 10.00 |
| Cedar wood oil | 10.00 |
| Cedrol cryst | 50.00 |
| Citral 10% in DPG | 10.00 |
| Citronellol | 5.00 |
| Coumarin | 10.00 |
| Cyclogalbanat ® 10% in DPG | 15.00 |
| Dihydromyrcenol | 80.00 |
| Farenal ® 10% in DPG | 5.00 |
| Galbex 10% in DPG | 25.00 |
| Geraniol | 80.00 |
| Geranyl nitrile | 40.00 |
| Hedion | 90.00 |
| Helional | 20.00 |
| Heliotropin | 5.00 |
| Hexenol cis-3 10% in DPG | 15.00 |
| Hexenyl salicylate cis-3 | 10.00 |
| Beta-ions | 5.00 |
| Iso E Super | 180.00 |
| Isodamascon ® 10% in DPG | 10.00 |
| Isogalbanate | 20.00 |
| Isoraldein 70 | 20.00 |
| Ketamber 10% in TEC | 25.00 |
| Lavandin oil Gross Nat. | 15.00 |
| Lilial | 20.00 |
| Linalool | 20.00 |
| Linalyl acetate | 40.00 |
| Brazilian Mandarin oil, green | 50.00 |
| Timberol ® | 40.00 |
| Vanillin | 5.00 |
| Veloutone 10% in DPG | 20.00 |
| Ysamber K ® | 10.00 |
| Total | 1000.00 |

DPG: dipropylene glycol,
TEC = triethyl citrate

Odor description of the perfume composition without additive: fresh, woody.

By adding 3 wt. % of ester from example 1, this perfume composition became fresher, more radiant, more rounded and more harmonious, a musk-like and sweet note being added and the woody and flowery aspects being intensified. Through their own odor and through their modifying and intensifying action (booster effect), the esters used lend the composition a unique character and unite the various olfactory elements.

EXAMPLE 8

Perfume Composition

| Constituent | wt.-‰ |
|---|---|
| Allyl cyclohexyl propionate | 3.00 |
| Amyl salicylate | 2.00 |
| Benzyl acetate | 64.00 |
| Citronellol | 122.00 |
| Citral 10% in DPG | 2.00 |
| Cyclamen aldehyde | 10.00 |
| Dihydromyrcenol | 3.00 |
| Dimethylbenzyl carbinyl acetate | 3.00 |
| Ethyl salicylate 10% in DPG | 2.00 |
| Eugenol | 3.00 |
| Indoflor 10% in DPG | 16.00 |
| Galbaniff | 164.00 |
| Geraniol | 35.00 |
| Dihydromethyljasmonate | 6.00 |
| Heliotropin | 4.00 |
| Hexyl cinnamaldehyde | 121.00 |
| Vertocitral | 4.00 |
| Hydroxycitronellal | 42.00 |
| Indol | 2.00 |
| Isobutyl salicylate | 6.00 |
| Lavandin Oil Grosso Nat. | 6.00 |
| Lactoscatone | 10.00 |
| Lilial | 190.00 |
| Linalool | 35.00 |
| Linalyl acetate | 10.00 |
| Methyl anthranilate 10% in DPG | 5.00 |
| Nerol | 10.00 |
| Orange oil | 6.00 |
| Paraxonal | 4.00 |
| Phenyl acetaldehyde dimethylacetal | 6.00 |
| Phenylethyl alcohol | 75.00 |
| Rosatol 10% in DPG | 6.00 |
| Sandalwood oil | 3.00 |
| Sandranol | 16.00 |
| TCD-Alcohol M | 2.00 |
| Trifernal | 2.00 |
| Total | 1000.00 |

DPG: dipropylene glycol

Odor description of the perfume composition without additive: flowery, lily of the valley.

This perfume composition is revitalized on adding 6 wt. % of ester from example 2. The impression of floweriness is greatly intensified. The composition has a more radiant, more rounded and more harmonious effect, with a musk-like and natural note being added. Through its own odor and through its modifying and intensifying action (booster effect), the ester used endows the composition with a unique character and unites the various olfactory elements.

EXAMPLE 9

Shampoo

A mixture of esters from example 1 was incorporated at a dosage of 0.5 wt. % in a shampoo basis of the following composition:

| | |
|---|---|
| Sodium lauryl ether sulfate (e.g. Texapon NSO, from Cognis Deutschland GmbH) | 12% |

| | |
|---|---|
| Cocamidopropyl betaine | 2% |
| (e.g. Dehyton K, from Cognis Deutschland GmbH) | |
| Sodium chloride | 1.4% |
| Citric acid | 1.3% |
| Phenoxyethanol, methyl, ethyl, butyl and propyl paraben | 0.5% |
| Water | 82.8% |

The pH of the shampoo basis was about 6. This was used for preparing 100 mL of a 20 wt. % aqueous shampoo solution. Two locks of hair were washed together for 2 minutes in this shampoo solution and then rinsed for 20 seconds under hand-hot running water. One lock of hair was wrapped wet in aluminum foil and the second lock of hair was dried with a hairdryer. Both locks of hair underwent olfactory testing by a panel.

Odor description in each case: very strongly radiant, musk-like, flowery, uplifting, softly woody, reminiscent of musk seeds.

EXAMPLE 10

Fabric Softener

The perfume composition from example 7 (after adding 3 wt. % of ester from example 1) was incorporated at a dosage of 0.5 wt. % in a fabric softener basis of the following composition:

| | |
|---|---|
| Quaternary ammonium methosulfate (Esterquat), approx. 90% | 5.5% |
| (e.g. Rewoquat WE 18, from Witco Surfactants GmbH) | |
| Alkyl dimethylbenzyl ammonium chloride, approx. 50% | 0.2% |
| (e.g. Preventol R50, from Bayer AG) | |
| Coloring solution, approx. 1% | 0.3% |
| Water | 94.0% |

The pH of the fabric softener basis was in the range from 2 to 3. Two pieces of cloth were rinsed with 370 g of a 1% aqueous fabric softener solution based on the fabric softener basis comprising 0.5% wt. % ester in a Linetest machine in the soft-rinse program for 30 minutes at 20° C. The cloths were wrung out and then spun for 20 seconds. One cloth was wrapped in cling film while wet, and one was hung up to dry. Then both cloths underwent olfactory testing by a panel.

Odor description in each case: flowery, woody, fresh, radiant, musk-like and woody aspects with light, sweet undertones, rounded and harmonious odor impression.

EXAMPLE 11

Washing Powder

The perfume oil composition from example 8 (after adding 6 wt. % of ester from example 2) was incorporated at a dosage of 0.4 wt. % in a washing powder basis of the following recipe:

| | |
|---|---|
| Linear Na-alkylbenzene sulfonate | 8.8% |
| Ethoxylated fatty alcohol C12-18 (7 EO) | 4.7% |
| Na-soap | 3.2% |
| Antifoaming agent | |
| DOW CORNING(R) 2-4248S POWDERED ANTIFOAM, silicone oil on zeolite as carrier material | 3.9% |
| Zeolite 4A | 28.3% |
| Na-carbonate | 11.6% |
| Na salt of a copolymer of acrylic and maleic acid (Sokalan CP5) | 2.4% |
| Na-silicate | 3.0% |
| Carboxymethylcellulose | 1.2% |
| Dequest 2066 ([[(phosphonomethyl)imino]bis[(ethylene-nitrilo)bis (methylene)]]tetrakis-phosphonic acid, sodium salt) | 2.8% |
| Optical brightener | 0.2% |
| Na-sulfate | 6.5% |
| Protease | 0.4% |
| Sodium perborate tetrahydrate | 22.0% |
| TAED | 1.0% |

Two pieces of cloth were washed with 370 g of a 1% aqueous washing powder solution based on 0.4 wt. % of the perfume oil composition from example 8 comprising washing powder basis (the pH of the washing powder lye is well into the basic range) in a Linetest machine in the main wash cycle for 45 minutes at 60° C. The cloths were first rinsed for 5 minutes with cold water, wrung out and then spun for 20 seconds. One cloth was wrapped in cling film while wet, and one was hung up to dry. Then both cloths underwent olfactory testing by a panel.

Odor description in each case: strongly flowery, radiant, musk-like and natural note with light sweet and woody undertones, rounded and harmonious odor impression.

The invention claimed is:

1. A compound of general formula (A)

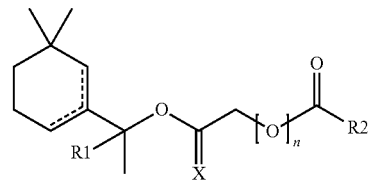

wherein
- - - - =saturated or unsaturated,
R1=H, methyl or ethyl
X=oxygen or dimethyl
n=0 or 1,
and for the case when n=1, R2 represents
(i) a CH2-O—R3 group, wherein R3=an alkyl group with 1 to 4 carbon atoms with a straight, branched or cyclic and saturated or unsaturated chain, or
(ii) a carbonyl-R3 group, wherein R3=an alkyl group with 1 to 4 carbon atoms with a straight, branched or cyclic and saturated or unsaturated chain, or
(iii) a CH2-carbonyl-O—R3 group, wherein R3=an alkyl group with 1 to 4 carbon atoms with a straight, branched or cyclic and saturated or unsaturated chain, or for the case when n=0, R2 represents
(iv) a CH2-O—R3 group, wherein R3=an alkyl group with 1 to 4 carbon atoms with a straight, branched or cyclic and saturated or unsaturated chain.

2. The compound according to claim 1, wherein R1=H and/or R3 is selected from the group consisting of methyl, ethyl, n-propyl and i-propyl.

3. The compound according to claim 1 selected from the group consisting of methoxyacetic acid-2-[1-(3,3-dimethyl-cyclohexyl)-ethoxy]-2-methyl-propyl ester, ethyl carbonic acid -2-[1-(3,3-dimethyl-cyclohexyl)-ethoxy]-2-methyl-propyl ester, propyl carbonic acid -2-[1-(3,3-dimethyl-cyclohexyl)-ethoxy]-2-methyl-propyl ester, methoxyacetic acid-1-(3,3-dimethyl-cyclohexyl)-ethoxycarbonylmethyl ester, ethyl carbonic acid -1-(3,3-dimethyl-cyclohexyl)-ethoxycarbonylmethyl ester, 4-methoxy-3-oxo-butyric acid-1-(3,3-dimethyl-cyclohexyl)-ethyl ester and 3-oxo-hexanoic acid-3,3-dimethyl-cyclohexyl)-ethyl ester.

4. A perfume mixture comprising a compound or a mixture of compounds according to claim 1 and one or more further perfumes, wherein the amount of the compound or mixture of compounds according to claim 1 is sufficient to impart or intensify a flowery note to the perfume mixture.

5. The perfume mixture according to claim 4, wherein one or more of the further perfumes are selected independently of one another from perfumes with one, several or all notes selected from the group consisting of flowery, woody, green-fruity, spicy-balsamic and musk-like.

6. The perfume mixture according to claim 5 comprising as further perfume at least one perfume with the note flowery.

7. The perfume mixture according to claim 5, wherein the mass ratio of all of the compounds or mixture of compounds to the total of the further perfumes contained in the perfume mixture is 1:1000 to 1:0.5.

8. The perfume mixture according to claim 4 comprising as further perfume at least one perfume with the note flowery.

9. The perfume mixture according to claim 8, wherein the mass ratio of all of the compounds or mixture of compounds to the total of the further perfumes contained in the perfume mixture is 1:1000 to 1:0.5.

10. The perfume mixture according to claim 4, wherein the mass ratio of all of the compound or mixture of compounds to the total of the further perfumes contained in the perfume mixture is 1:1000 to 1:0.5.

11. The perfume mixture according to claim 4, wherein the compound or mixture of compounds is 0.00001 to 99.9 wt. %, relative to the total weight of the perfume mixture.

12. The perfume mixture of claim 4 in the form of an oil.

13. The perfume mixture according to claim 4, wherein the proportion of all of the compounds or mixture of compounds is 0.001 to 70 wt. %, relative to the total weight of the perfume mixture.

14. The perfume mixture according to claim 4, wherein the proportion of all of the compounds or mixture of compounds is 0.01 to 50 wt. %, relative to the total weight of the perfume mixture.

15. A perfumed article, comprising a perfume mixture according to claim 4 in a sensorially effective amount.

16. A perfumed article, comprising a compound or a mixture of compounds according to claim 1 in a sensorially effective amount.

17. The perfumed article according to claim 16, selected from the group consisting of perfume extracts, eau de parfum, eau de toilette, aftershave, eau de cologne, pre-shave products, splash-cologne, perfumed tissue wipes, acidic, alkaline and neutral cleaning agents, textile fresheners, ironing aids, liquid detergents, powder detergents, laundry pretreatment agents, fabric softeners, washing soaps, washing tablets, disinfectants, in particular surface disinfectants, air fresheners, aerosol sprays, waxes, polishes, body care products, hand creams and lotions, foot creams and lotions, depilatory creams and lotions, after-shave creams and lotions, tanning creams and lotions, hair care products, deodorants and antiperspirants, candles, lamp oils, joss sticks, insecticides, repellents and propellants.

18. A method of producing a perfume mixture or a perfumed product, comprising:
  a) providing a compound or a mixture of compounds of claim 1;
  b) providing further constituents of a perfume mixture or of a perfumed product; and
  c) bringing the constituents from b) in contact with a sufficient amount of the constituent or constituents from a) for sensorially effective imparting or intensifying of an odor note musk-like in combination with imparting or intensifying the odor note flowery while simultaneously imparting or intensifying the odor impression radiant.

* * * * *